United States Patent [19]

Boniver

[11] Patent Number: 5,128,126
[45] Date of Patent: Jul. 7, 1992

[54] USE OF PHARMACEUTICAL COMPOSITIONS CONTAINING AT LEAST ONE CYTOKINE FOR THE SYSTEMIC TREATMENT OF PRENEOPLASTIC LESIONS

[75] Inventor: Jacques Boniver, Heusy-Verviers, Belgium

[73] Assignee: Boehringer Ingelheim International GmbH, Fed. Rep. of Germany

[21] Appl. No.: 505,269

[22] Filed: Apr. 9, 1990

[30] Foreign Application Priority Data

Apr. 11, 1989 [DE] Fed. Rep. of Germany ....... 3911720
Feb. 21, 1990 [DE] Fed. Rep. of Germany ....... 4005416

[51] Int. Cl.5 .................... A61K 37/02; A61K 37/66
[52] U.S. Cl. ................... 424/85.5; 424/85.1; 424/85.2; 424/85.4

[58] Field of Search .............. 424/85.1, 85.4, 85.5, 424/85.6, 85.7, 85.2

[56] References Cited

U.S. PATENT DOCUMENTS 4,791,101 12/1988 Adolf ..................... 424/85.1

Primary Examiner—Merrell C. Cashion, Jr.
Assistant Examiner—Choon Koh
Attorney, Agent, or Firm—Sterne, Kessler, Goldstein & Fox

[57] ABSTRACT

The invention relates to the use of pharmaceutical compositions containing at least one cytokine for the systemic treatment of preneoplastic lesions. The pharmaceutical composition according to the invention may contain interferon, tumor necrosis factor, or a combination of both interferon and tumor necrosis factor.

11 Claims, 1 Drawing Sheet

USE OF PHARMACEUTICAL COMPOSITIONS CONTAINING AT LEAST ONE CYTOKINE FOR THE SYSTEMIC TREATMENT OF PRENEOPLASTIC LESIONS

FIELD OF THE INVENTION

The present invention relates to the use of pharmaceutical compositions for the systemic therapeutic and prophylactic treatment of preneoplastic lesions, containing as active substance at least one cytokine, preferably at least one interferon (IFN) or a tumour necrosis factor (TNF) or a combination of these two cytokines, for example IFN-gamma (IFNγ) or TNF alpha (TNFα) or a combination thereof.

BACKGROUND OF THE INVENTION

The use of these pharmaceutical compositions according to the invention is directed particularly against preneoplastic lesions which have not or not yet manifested themselves clinically or morphologically and which are causally connected with an exposure to or treatment by physical and/or chemical agents in mammals, particularly humans, and may result in malignant degeneration.

As far as is known, cytokines have hitherto been used systemically only for treating manifest cancers or tumours, i.e. after neoplastic transformation of certain types of cells or tissue has taken place, and in some cases an effect has been shown in vitro and in vivo (Berry, S. F. et al., J. Immunol. 135, 1165–1171, 1985; Ruddle N. H., Immunol. today 8, 129, 1987; Bentler B. & Cerami, A., New Engl. J. Medicine 316, 379–382, 1987).

It is also known to use interferon-containing gels either locally or topically for treating existing precancerous changes in external tissue areas such as the skin or mucous membranes (WO 83/01198). Systemic treatment is regarded as being ineffective or, on account of the possibility of an excessively high dosage, disadvantageous or harmful. The teaching of WO 83/01198 is taken up by U.S. Pat. No. 4,605,555, which also discloses the exclusively external, i.e. topical or local administration of interferon-containing gels, ointments, pastes, liquids or sprays.

Since the fight against existing cancers, even using the more modern methods, has not hitherto shown the levels of success hoped for, particular significance must be accorded to the treatment of preneoplastic lesions, and particularly the prevention or interruption of the process of neoplastic transformation.

SUMMARY OF THE INVENTION

The aim of the present invention was therefore to provide agents which will enable systemic therapeutic and prophylactic treatment of preneoplastic lesions, with the objective of preventing or interrupting the process of transformation into a malignant tumour.

Figure 1:
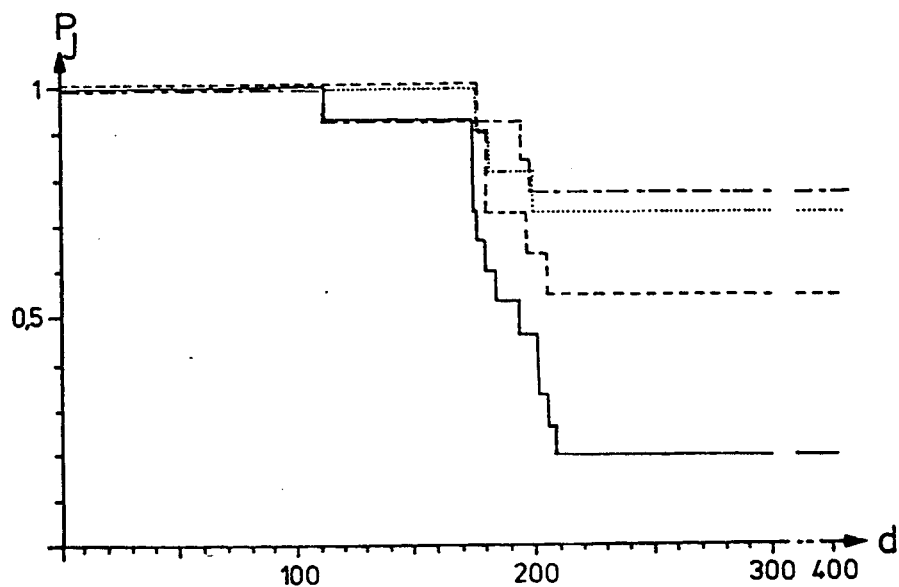
FIG. 1. Survival curve of C57BL/Ka mice irradiated with 4×1.75 Gy:
Control (———) IFN-gamma (—————), TNF-alpha (———), IFN-gamma plus TNF-alpha (......)

As a solution to this problem it has surprisingly been found that the systemic use of cytokines, preferably IFN or TNF or a combination thereof, for example interferon-gamma (IFNγ) or tumour necrosis factor alpha (TNFα) or a combination thereof prevents the progression of preneoplastic cells, preferably those which are induced by physical or chemical influences, towards a transformation into malignant degeneration.

It was unexpectedly found that repeated injections of IFN, for example IFNγ, or TNF, for example TNFα or combinations thereof, prevents the development of lymphomas of the thymus in mice which had previously been exposed to a leukaemogenic irradiation using a known method (Kaplan H. S., Cancer Res. 27, 1325–1340, 1967, Defresne, M. P. et al., J. Nat. Cancer Inst. 77, 1079–1085, 1986). This clearly shows that, in addition to having their known antitumour effects in vitro and in vivo, these cytokines also act on preneoplastic tissue by the systemic route and interrupt the further process, which takes place in a number of steps, towards malignant degeneration, which would otherwise lead to the development of lymphomas. As far as is known, no such effect on preneoplastic cells has previously been described.

Accordingly, it could be postulated that IRN and/or TNF are capable of returning the preneoplastic cells into their original state.

By way of example, this effect was proved by the fact that it was possible to achieve a significant reduction in mortality and the occurrence of radiationinduced lymphomas of the thymus by the systemic use of IFNγ and/or TNFα.

The cytokines which are to be used according to the invention will therefore encompass all preneoplastic lesions which may be produced, in particular, by physical and/or chemical effects on a mammal and will progress into a malignant cancerous stage in all probability. The preneoplastic lesions which can be treated according to the invention will therefore include in particular those which occur especially in patients who have been receiving chemical and/or physical treatments are therefore exposed to a considerable risk of developing malignant tumours. In such patients there is the particular risk of developing myelodysplasic syndrome or acute myeloid leukaemia, which may occur after whole body radiation or after exposure to benzene or after treatment with alkylating agents for treating Hodgkin's disease (10% of these patients run the risk of acute leukaemia after chemotherapy), or other tumours such as ovarian tumours or lymphomas.

Therefore, all the cells and tissues of the external and internal organs or the superficial structures of the mammalian body or of man might be subject to the preneoplastic lesions which are to be treated according to the invention.

Accordingly, the crux of the present invention is the systemic use of a pharmaceutical composition for the therapeutic and/or prophylactic treatment of preneoplastic lesions, containing at least one cytokine or a combination of at least two cytokines. Preferably, the pharmaceutical composition which is to be administered systemically is for the treatment and/or prophylaxis of preneoplastic lesions which might be caused by physical and/or chemical effects on a mammalian organism.

The use according to the invention of the abovementioned cytokines which are to be administered systemically, either individually or in combination with one another, possibly in the form of a "kit-of-part", can therefore be regarded as being an adjuvant or prophylactic which can be administered before, during or immediately after physical and/or chemical therapy, in order to avert the formation of premeoplastic lesions and the malignant degeneration which develops therefrom, since preneoplastic lesions of this kind are generally not clinically or morphologically apparent.

The cytokines which are to be used according to the invention, particularly IFN and TNF, are known to the person skilled in the art and may be produced by methods known per se, advantageously using the method of DNA recombination.

For immunological reasons the person skilled in the art knows that species-specific active substances should preferably be used when biologically active substances native to the body are being used. For the species-specific use of cytokines according to the invention, therefore, the cytokine isolated from the particular species-specific tissues is preferred or else the nucleic acids (RNA, DNA) isolated from the species-specific tissues or cells in order to prepare the cytokine in question by DNA recombination, but more particularly the polypeptide which is identical to the genuine cytokine in question and has the known biological range of activity of the associated cytokine. The term cytokine is familiar to those in the art and includes for example the interleukins known in the art (e.g. IL-1, IL-2, IL-3, IL-4, IL-5), interferon (e.g. $\alpha$, $\beta$, $\gamma$), tumour necrosis factors (e.g. $\alpha$, $\beta$), macrophage-activating factors (MAF), migration inhibiting factors (MIF), growth factors (e.g. transforming growth factors $\alpha,\beta$).

Thus, for example, the IFN used on humans for the purposes of the invention will be a human IFN, more particularly human-IFN$\gamma$, and TNF will be a human TNF, particularly human-TNF$\alpha$.

The compositions are administered according to the invention by the systemic routes known per se, e.g. continuously, for example using micropumps, intermittently or in the form of a bolus. The dosage of the cytokines will be guided by the systemic applications used hitherto, and will be adjusted individually to suit the gravity of the disease, the response rate and the further progress of the disease.

Generally speaking, the quantity of active substance to be administered will be in the range from $10^2$ to $10^8$ IU, preferably from $10^4$ to $10^6$ IU.

The preparations to be administered may be produced using the excipients, stabilisers and carriers available in the art, such as albumin, electrolytes, injectable solutions or solutions for infusion.

EXAMPLE

The Example which follows is intended to illustrate the invention without restricting its scope:

Female mice five to six weeks old (C57BL/Ka, Stanford University, Calif.) were irradiated over their whole bodies with 4 doses of 1.75 Gy each at weekly intervals (Stabilivolt Siemens, 190 Kv, 18 mA, 0.5 mm Cu filter, focal distance 35 cm, dose rate 1.6 Gy/mm).

Murine IFN$\gamma$, prepared by DNA recombination, Messrs. Genentech, South San Francisco (Calif.), or prepared for example by the method of Gray P. W., Goeddel, D. V., Proc.Natl. Acad. Sci. USA, 80, 5842–5846, 1983, with a specific activity of $2\times10^7$ U/mg and human TNF-$\alpha$, prepared by DNA recombination using known methods, with a specific activity of $6\times10^7$ U/mg, were diluted in RPMI 1640 medium supplemented with 10% foetal calves' serum. Of this dilution, 200 $\mu$l aliquots containing either $4\times10^4$ U IFN$\gamma$ or $2.5\times10^5$ U TNF$\alpha$ or a mixture thereof, were injected intraperitoneally on the first day after the last irradiation with 1.75 Gy. Three injections were given per week (every alternate day) within the first 6 weeks.

Each of the three groups contained 16 mice and the irradiated group given no treatment also contained 16 control animals.

Figure 2:
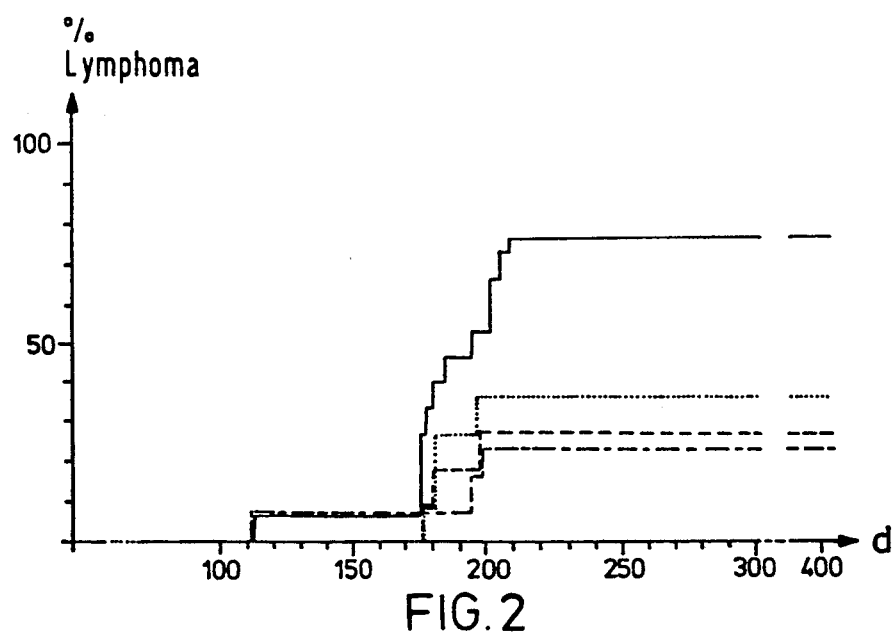
FIG. 2. Cumulative occurrence of lymphomas in C57BL/Ka mice irradiated with 4×1.75 Gy:
Control (———) IFN-gamma (—————), TNF-alpha (———), IFN-gamma plus TNF-alpha (......).

The survival curve was plotted according to Kaplan G. L. & Meier, P., J. Am. Statist. Assoc. 53, 457–481, 1958. The Mantel-Haenzael test was used to compare the differences between the various groups. The curves in FIGS. 1 and 2 show the survival and the formation of lymphomas in the irradiated mice treated with IFN$\gamma$ and TNF$\alpha$, compared with the control group. In the three groups treated with cytokine injections, the occurrence of lymphomas of the thymus was significantly lower than in the untreated mice which had merely been irradiated ($P<0.05$). Similar results were obtained for the survival rate.

I claim:

1. A method for treating preneoplastic lesions comprising administering systemically to an animal in need of such treatment an effective amount of at least one cytokine.

2. The method of claim 1 wherein said preneoplastic lesion is chemically caused.

3. The method of claim 1 wherein said preneoplastic lesion is caused by irradiation.

4. The method of claim 1 wherein said preneoplastic lesion is chemically caused and caused by irradiation.

5. The method of claim 1 wherein said cytokine is interferon.

6. The method of claim 1 wherein said cytokine is tumor necrosis factor.

7. The method of claim 1 wherein said method comprises treatment with at least two cytokines.

8. The method of claim 7 wherein one of said two cytokines is interferon and the other of said two cytokines is tumor necrosis factor.

9. The method of claim 1 wherein said cytokine has $10^2$ to $10^8$ IU.

10. The method of claim 1 wherein said cytokine is isolated from a cell which naturally produces said cytokine.

11. The method of claim 1 wherein said cytokine is obtained from a cell transfected with a heterologous nucleic acid sequence which specifies said cytokine.

* * * * *

UNITED STATES PATENT AND TRADEMARK OFFICE
CERTIFICATE OF CORRECTION

PATENT NO. : 5,128,126

DATED : July 7, 1992

INVENTOR(S) : Jacques Boniver

It is certified that error appears in the above-identified patent and that said Letters Patent is hereby corrected as shown below:

Column 2, line 28, "IRN" should read "IFN".

Signed and Sealed this

Twenty-fourth Day of August, 1993

*Attest:*

BRUCE LEHMAN

*Attesting Officer*     *Commissioner of Patents and Trademarks*